(12) United States Patent
Donnelly et al.

(10) Patent No.: US 11,769,320 B2
(45) Date of Patent: Sep. 26, 2023

(54) SYSTEMS AND METHODS FOR DYNAMIC IDENTIFICATION OF A SURGICAL TRAY AND THE ITEMS CONTAINED THEREON

(71) Applicant: Ortelligence, Inc., West Chester, PA (US)

(72) Inventors: Timothy Donnelly, Glen Mills, PA (US); Simon Greenman, London (GB); Piotr Banasiński, Łódź (PL)

(73) Assignee: Ortelligence, Inc., West Chester, PA (US)

( * ) Notice: Subject to any disclaimer, the term of this patent is extended or adjusted under 35 U.S.C. 154(b) by 16 days.

(21) Appl. No.: 17/693,563

(22) Filed: Mar. 14, 2022

(65) Prior Publication Data

US 2022/0292815 A1 Sep. 15, 2022

Related U.S. Application Data

(60) Provisional application No. 63/161,270, filed on Mar. 15, 2021.

(51) Int. Cl.
*G06V 10/774* (2022.01)
*G06V 20/64* (2022.01)
*G16H 40/40* (2018.01)

(52) U.S. Cl.
CPC .......... *G06V 10/774* (2022.01); *G06V 20/647* (2022.01); *G16H 40/40* (2018.01); *G06V 2201/034* (2022.01)

(58) Field of Classification Search
CPC .............................................. G06V 2201/034
See application file for complete search history.

(56) References Cited

U.S. PATENT DOCUMENTS

2009/0116747 A1 5/2009 Duong et al.
2009/0317002 A1 12/2009 Dein
(Continued)

OTHER PUBLICATIONS

Rupp et al. "Effectiveness of a radiofrequency detection system as an adjunct to manual counting protocols for tracking surgical sponges: a prospective trial of 2,285 patients." Journal of the American College of Surgeons 215.4 (2012): 524-533. Jun. 5, 2012 (May 6, 2012) Retrieved on Jun. 8, 2022 (Aug. 6, 2022) from https://www.sciencedirect.com/science/article/abs/pii/S1072751512004899.

*Primary Examiner* — Ross Varndell
(74) *Attorney, Agent, or Firm* — Stradley Ronon Stevens & Young, LLP; Philip J. Foret; David P. Fitzgibbon

(57) ABSTRACT

The invention provides artificial intelligence-enabled image recognition methods and systems for continuously training a computer system to accurately identify a surgical item in a tray using at least 100 randomly created 2-dimensional images of a 3-dimensional synthetic item having unique identifiers assigned to the images or item. The invention also provides an artificial intelligence-enabled image recognition method and system for use to determine whether surgical instruments are present or missing on a surgical tray, and, if applicable, identifying those missing. In one aspect, a server receives an image and analyzes the image with a deep convolutional neural network to classify the type of tray and then compares a list of items that should be on the tray to that which the computer recognizes on the tray to generate an output displayed to a user identifying the items present and/or missing.

12 Claims, 6 Drawing Sheets

(56) References Cited

U.S. PATENT DOCUMENTS

| | | |
|---|---|---|
| 2017/0061625 A1 | 3/2017 | Estrada et al. |
| 2017/0169620 A1 | 6/2017 | Bleiweiss et al. |
| 2018/0204323 A1* | 7/2018 | Sayani ................ G06Q 10/087 |
| 2020/0143195 A1 | 5/2020 | Montano |
| 2021/0209449 A1* | 7/2021 | Neagovici ................ G06T 7/11 |
| 2021/0236227 A1* | 8/2021 | Kumar ................... A61B 90/08 |
| 2023/0131623 A1* | 4/2023 | Dal Mutto .............. G06T 17/00 |
| | | 382/100 |

* cited by examiner

SYSTEMS AND METHODS FOR DYNAMIC IDENTIFICATION OF A SURGICAL TRAY AND THE ITEMS CONTAINED THEREON

RELATED APPLICATIONS

This application claims the priority and benefit of U.S. Provisional Patent Application Ser. No. 63/161,270, titled "Systems and Methods for Dynamic Identification of a Surgical Tray and the Items Contained Thereon," filed on Mar. 15, 2021, the contents of which are incorporated by reference in their entirety into this application.

FIELD OF THE INVENTION

Aspects of embodiments of the present invention relate to the field of computer vision and including systems and methods configured to automatically and accurately: identify, confirm, and track surgical trays and contents therein, as the trays and contents move through the operation theater and to notify a user, e.g., medical personnel, if one or more items on the trays is missing.

BACKGROUND

Surgery requires a specific set, or sets, of items to carry out. Some of the items include instruments needed to perform the surgery (e.g., drill bits, scissors, scalpels, etc.), while other items are devices or implants designed to replace, support, or enhance an existing biological structure. All items must be sterilized and placed on specific surgical trays before the items are moved into the operating room. After the surgery is completed, used and unused items are removed from the operating room in the same or different condition, configuration, or, in some instances, on a different tray from which the items were placed before the surgery. For example, certain of the items may have biological material, such as blood, on their surfaces. In addition, members of the surgical team may place used items on top of each other on a tray, thereby partially blocking the view of certain items. It is commonplace for the items on trays coming out of the operating room to look different, and less ordered, than going into the operating room. Regardless, it is important to identify and track all necessary items going into the operating room and all items leaving the operating room.

Keeping track of the items on trays is tedious and requires substantial amounts of time and concentration of personnel tasked with tracking the items and trays. Hospitals use protocols and procedures, which require an individual to count all the surgical instruments going into and coming out of the surgery. Conventional protocols require visual confirmation and/or manual handling of each instrument separately to facilitate a count. This approach is slow, prone to human error, and inefficient.

Imaging technology, which can include an artificial intelligence (AI) system using computer vision, has been proposed to track surgical items. Such proposed AI-enabled systems, to date, do not provide a solution because such systems are not properly trained to accurately identify a tray and its contents. No solution exists for training a dataset large enough to use computer vision systems to accurately identify trays and items on the tray because such dataset requires numerous images of real-world items presented at different angles, under various lighting conditions, and/or partially covered by other items to reflect how an item might be seen in the real-world use. Massive amounts of time would be needed to simply create the necessary training dataset populated with hundreds of thousands of real-world images of instruments at all different angles, light intensities, occlusion levels, etc. Time limitations render the building of training datasets for an AI system impractical. Consequently, the proposed AI-enabled systems do not solve the problems inherent to convention protocols for identifying and tracking surgical items on a tray(s).

The real-world, temporal limitation significantly hinders an AI-based system's learning and negatively impacts the system's recall ability, i.e., how often the system needs to guess at what an item is, as well as its precision, i.e., how often the system correctly guesses an item. To date, it has not been feasible to create a workable dataset from which an AI-enabled computer vision system can learn to identify items on a surgical tray. Such a workable database requires hundreds of thousands of real-world images of each one of the items to be placed on the tray. A more streamlined solution for training an AI-enabled computer vision system is needed.

One proposed shortcut to work around the feasibility issue involves the use of tray and instrument markers. With this shortcut, an AI-enabled system must learn only the markers, not the items themselves. For example, U.S. Pat. No. 10,357,325 proposes use of a camera to identify: (1) a tray based on a matrix code (e.g., bar or QR code) present on the tray, and (2) instruments on the tray based on color markers (e.g., colored tape, bands, or rings) affixed to the instrument(s). The problems with such a marker-based approach is the number of different surgical items and manufacturers, which must be marked and coded, as well as lack of sufficient, reliable workability in an operating room. Furthermore, surgeries occur at all times of day and night, which changes the nature of lighting exposure to the items on a tray as they enter and leave the operating room. The lighting changes can cause an automatic imager, such as a camera, to read a color marker as one hue going into the operating room but a different hue coming out. Consequently, the marker-based approach would fail if one or more of the following occurs: (1) the tray lacks a specific matrix identifying the tray or the matrix is blocked from view, (2) instruments are not returned to (a) their original slots on the same tray, (b) their original orientation in the same tray, or (c) the same tray, or (3) the color markers on the items are obscured from view, appear as different hues under different lighting conditions, or even fall off an item.

Consequently, there is a present need for a system and method to train an artificial intelligence (AI)-enabled computer vision system to recognize the items on a surgical tray, automatically and accurately: (1) without the need for independent markers or codes affixed to the tray or items in the tray, (2) regardless of various lighting conditions, and (3) that is unaffected by the location, angle, condition, or occlusion percentage of the items on the tray. There is also a present need for a system and method using a trained AI-enabled, computer vision system to accurately identify items on a tray with high recall and precision.

SUMMARY

The invention meets the present needs by providing an AI-enabled, dynamic, computer vision system useful for identifying surgical trays, instruments, and implants. The AI-enabled system of the invention is trained to meet a minimum recall and precision threshold previously upload by an administrator of the system or an employee, contractor, or agent of the administrator. Once trained, the AI-enabled system is configured to be deployed for use in a manner that permits a user to take a picture, video, or image of at least one surgical tool tray with a mobile computer device, which includes an imager (e.g., a camera) and then the system notifies the user of: (1) the types of tray(s), (2) the instruments and implants on the tray(s), and/or (3) any instruments and implants missing from tray(s). In embodiments, the system permits a user to take another picture, video, or image of the tray(s) after surgery, and then the system notifies the user, and records into a database of the system, which instruments and implants are present on the tray(s).

In general, the systems and methods of the invention provide for training an AI-enable, computer vision system by: (1) scanning a surgical instrument or tray at least two times to create a preliminary 3-D synthetic model of the item; (2) revising the preliminary 3-D synthetic model to create a final 3-D synthetic item that exists entirely in the virtual world but whose attributes, such as reflectivity or shape, mimic the real-world attributes of the item; (3) assigning a unique identification to the final 3-D synthetic item; (4) creating an infinite training set of 2-dimensional images of the final 3-D synthetic item for which a computer vision assisted AI platform can learn from by varying: (a) orientation of the virtual item, (b) the virtual light color/intensity hitting the virtual item, (c) how much of the virtual item is blocked from view, (d) the elevation of the virtual item above an identified surface, (e) the virtual blurring of the surfaces of the virtual item with virtual biological material, etc.; (5) providing the training set to the system until the system identifies at least one pattern in the training set and creates/amends at least one identification model attributable to the pattern; (6) creating a unique test set where the system provides a numeric confidence factor representing the confidence the system has that the identification of the item is correct; (7) determining if the system correctly identified the item in the test set and whether the confidence factor is equal to or greater than the desired confidence factor and to the extent the item was misidentified or the confidence factor is not at or above the desired threshold repeating steps 4-7 until the identification of the item and confidence threshold are met if the system passed uploading an updated model for identifying the item to a server for later use.

In general, the systems and methods of the invention provide for using an AI-enable, computer vision system by: (1) receiving an image of the surgical tray and items contained thereon; (2) launching a plurality of tray classification models comprised of tensors, wherein the tray classification models have been previously uploaded as outlined above in the training case section; (3) analyzing the image and classifying the type of tray in the image based on the tray classification models; (4) upon classifying the tray, calling up from the database a plurality of instrument identification models linked to the classification of the tray wherein the instrument identification models were uploaded as outlined above in the training case section; (5) analyzing the image and identifying the type of items in the image based on the instrument identification models; (6) comparing the classified items to the list of items linked to the classified tray to determine any missing items, and (7) notifying the software application of the classified items and any missing items.

In an exemplary, non-limiting embodiment of the invention, a system is provided that is configured to be trained to classify a surgical tray and identify items contained thereon. The system includes a processor in communication through a wired and/or wireless communication network with a software application, as well as an imager and server. The imager may be a camera capable of taking pictures or video. In embodiments, the imager creates files of visual depictions of a real-world scene using pixels and/or vectors. For example, the camera may be capable of producing images in any one or more of the following file formats: JPEG (or JPG)—Joint Photographic Experts Group, PNG—Portable Network Graphics, GIF—Graphics Interchange Format, TIFF—Tagged Image File, PSD—Photoshop Document, PDF—Portable Document Format, EPS—Encapsulated Postscript, AI—Adobe Illustrator Document, INDD—Adobe Indesign Document, or RAW—Raw Image Formats.

The system of the invention utilizes synthetic images of trays and items to create a preliminary 3-dimensional model of the tray or surgical instrument. This approach enables the creation of a workable training dataset of synthetic images. In a non-limiting embodiment, the system of the invention is configured to permit an administrator of the system, or an employee, contractor, or agent of the administrator, to scan a tray or surgical instrument, implant, tool or fastener with an imager at least two times to create a preliminary 3-dimensional model of the tray or surgical instrument and then use a software application to revise the preliminary 3-dimensional model of the tray or surgical instrument, implant, tool, or fastener, to create a final 3-dimensional synthetic item file for each surgical instrument, implant, tool, or fastener. The software application allows revisions to the final 3-dimensional synthetic item including defining at least one element selected from a list consisting of: geometry, position of each vertex, UV position of each texture coordinate vertex, vertex normals, faces that make each polygon defined as a list of vertices, and texture coordinates for the item. The software application assigns a unique identification to the final 3-dimensional synthetic model, also referred to as a "3-dimensional synthetic item." The unique identifications can be alphanumeric and/or colorimetric. In an embodiment, the software application can link the unique identification to one or more tray classifications in an uploaded image. The tray classification can include a predefined list of the instruments, implants, tools, fasteners, or other objects linked to the tray, which the system may identify.

Next, the system of the invention is configured to automatically create a training dataset and a test dataset, each of which are derived for each final 3-dimensional synthetic item. The training data set is linked to the unique identification, assigned by the software, to enable the system to learn from the final 3-dimensional synthetic item. Conversely, the test dataset does not include a link to the unique identification. All datasets, i.e., training dataset(s) and test dataset(s), are comprised of unique synthetic images of the final 3-dimensional synthetic item, wherein the orientation of the final 3-dimensional synthetic item, the synthetic light color or intensity illuminating the final 3-D synthetic item, or the elevation of the final 3-dimensional synthetic item above an identified surface are unique in each image. In certain embodiments, the training dataset(s) may also include up to 100 or more real world images of a tray, surgical tool, implant, fastener, or other object. The unique training dataset for each 3-dimensional synthetic item can contain hundreds of thousands of unique 2-dimensional images of a 3-dimensional synthetic item, and, optionally, numerous real-world images of the object scanned to create the 3-dimensional synthetic item, all of which can be used to in the training process for an AI-enable computer vision system of the invention to recognize each 3-dimensional synthetic item with a high percentage of recall and precision. Each training dataset can be created efficiently by the system and methods of the invention. One feature of the invention is that training of the system can be ongoing to continuously improve recall and precision through use of up to an infinite number of synthetic training images of the 3-dimensional synthetic item in the training dataset.

The system and method of the invention can be trained by each training dataset of a 3-dimensional synthetic item, which contains 2-dimensional images and unique identifications of a tray, or surgical tool, implant, fastener, or other object in or on the tray. The system is configured to process each 2-dimensional image in the training dataset and create and update an identification model, which may be deployed for use to identify the tray or tray, surgical tool, implant, fastener, or other object on or in the tray without the need for the correct identification provided with the training dataset. The identification model includes feature vectors attributable to visual patterns of a tray or surgical tool, implant, fastener, or other object identified in each training dataset. The feature vectors can be combined into matrices to provide a 2-dimensional array of feature vectors. The matrices can be layered into tensors to provide a 3-dimensional array to be used by the system to classify a tray(s) or identify an instrument(s) when the system is deployed in the surgical theater.

Once created, each identification model for a 3-dimensional synthetic item, which comprise a tensor(s) attributable to known tray(s) and surgical tool, implant, fastener, or other object on or in a tray, are stored on a server at a site where the final 3-dimensional synthetic items are located or at a location remote from the final 3-dimensional synthetic items. While the system processes additional training dataset(s), the system can create at least one additional feature vector(s) attributable to a known or new pattern of the final 3-dimensional synthetic item. Such additional feature vector(s) can be combined to create new matrices or added to preexisting matrices in the relevant identification model. The addition or revision of matrices in the identification model can be used to revise or create new tensor(s), which are then uploaded by the system to the server or uploaded to a second server for later deployment for use. This creation of a feature vector(s) to build tensor(s) attributable to an identified pattern(s) of a surgical tool(s), an implant(s), a fastener(s), or other object(s) trains the system so that the system is capable of automatically recognizing the same instruments in different images when the system in deployed for use with new or updated identification model(s).

Each test dataset for a 3-dimensional synthetic item can be used to evaluate the amount and effectiveness of training the system has undergone. A test dataset can be provided to the system during or after the related training dataset is provided to the system to be processed. The system is provided with answers when processing the training dataset(s), but the system is not provided with answers when processing the test dataset(s). When each synthetic image in a test dataset is provided to the system, the system identifies the item in the synthetic image and provides a numeric confidence factor, which represents the confidence the system has that the identification of the item is correct. If the numeric confidence factor fails to meet, or exceed, a minimum threshold previously set in the system by the administrator of the system, or an employee, contractor, or agent of the administrator, additional training dataset(s) are provided to the system so that the system can improve the confidence factor by creating updated feature vector(s) attributable to the identified pattern to be stored on the server(s) for later deployment. Conversely, if the system identification(s) and numeric confidence value(s) is correct, and the confidence factor is equal to or greater than confidence factor set in the system, then the system can be deployed for use with the new or updated identification model(s).

In certain embodiments, even after the system is deployed for use with new or updated identification model(s), additional training dataset(s) can be continuously provided to the system to continuously create feature vector(s) attributable to the identified pattern to increase the recall and precision values of the system when tested on unique images (synthetic or real-world) with greater than a minimum threshold previously identified by the administrator of the system, or an employee, contractor, or agent of the administrator.

In an exemplary, non-limiting embodiment, the deployed system of the invention comprises a software application. The application is configured to operate on a mobile computer device or on a computer device, either of which is in communication with at least one image data collection device configured to produce an image of the surgical tray. The application is configured to receive the image of the surgical tray or surgical tool, implant, fastener, or other object on or in the surgical tray from the image data collection device, and to communicate the image through a wired and/or wireless communication network to a server located at a site where the surgical tray is located or at a location remote from the site. The system includes a processor in communication through the wired and/or wireless communication network with the software application, as well as the server, of the system. The processer is configured to call up from a library database of the system, upon communication of the image to the server: a plurality of previously created identification model(s) comprised of previously created tensors linked to synthetic trays. The identification model(s) linked to the synthetic trays were previously uploaded by the training system previously described. The processor is configured to analyze the image and classify the type of tray in the image based on the identification model(s) linked to synthetic trays. Then, based on the classification of the tray in the image assigned by the processor, the processor calls up from the library database: (1) a plurality of identification model(s) linked to 3-dimensional synthetic items, which are linked to the classification of the tray, (2) the identification model(s) including: (a) surface texture, (b) item material composition, and (c) a size tolerance; (3) a list of items linked to the synthetic tray, and (4) a plurality of feature vector(s) created for 3-dimensional synthetic items as outlined above. The processor then analyzes the images and proceeds to classify the type of items in the image based on the identification model(s) linked to the 3-dimensional synthetic items. The processor then compares the list of classified items to the list of items linked to the classified tray to determine if there are any missing items. The system notifies the software application of the classified items and any missing items. The software application then displays the list of identified and missing items.

In other embodiments, a method for identifying a surgical tray and objects contained thereon, is disclosed. The method comprises first receiving an image (photograph or video) of the surgical tray and objects contained thereon, from an image data collector, e.g., a camera. The image data collection device is connected to a server or a remote server using a software application operating on a mobile computer device or a computer device that may be synced with the mobile computer device. The mobile computer device or the computer device communicate through a wired and/or wireless communication network with the server at a site where the image is taken or with a remote server in a location that is remote to the site and in communication with the server. Upon receiving the information, the method includes calling up from a database, using a processor: a plurality of identification model(s) linked to synthetic trays. Again, the identification model(s) have been previously obtained by training an AI-based computer vision system in the manner previously discussed. Next, the method includes analyzing the image and classifying the type of tray in the image based on the identification model(s) linked to the synthetic trays. Upon classifying the tray, the method includes calling up from the database a plurality of identification model(s) linked to 3-dimensional synthetic items, which are included in the classification of the tray, the identification model(s) including: (a) surface texture, (b) item material composition, and (c) a size tolerance; and (d) a list of 3-dimensional synthetic items linked to the identified tray classification. Again, the identification model(s) linked to the 3-dimensional synthetic items had been created by training an AI-based computer vision system and the list linking 3-dimensional synthetic items to synthetic trays has been previously uploaded by a professional with knowledge of the items intended to be contained on the tray. Then, the method includes analyzing the image and classify the type of items in the image based on the identification model(s) linked to the 3-dimensional synthetic items. Next, the method includes comparing the classified items to the list of items linked to the classified tray to determine any missing items. Then, the method includes notifying the software application of the classified items and any missing items. Finally, the method includes displaying the results on a display to a user of a mobile computer device.

In certain embodiments, the image data collection device is a camera and may be mounted on a wearable device.

These and other features, aspects, and advantages of the present invention will become better understood with reference to the following description and appended claims.

BRIEF DESCRIPTION OF THE FIGURES

Additional aspects, features, and advantages of the invention, as to its system, architecture, components, configuration, and functionality will be understood and become clear when the invention is considered considering the following description of the figures made in conjunction with the accompanying drawings, wherein.

DETAILED DESCRIPTION

Figure 1A:
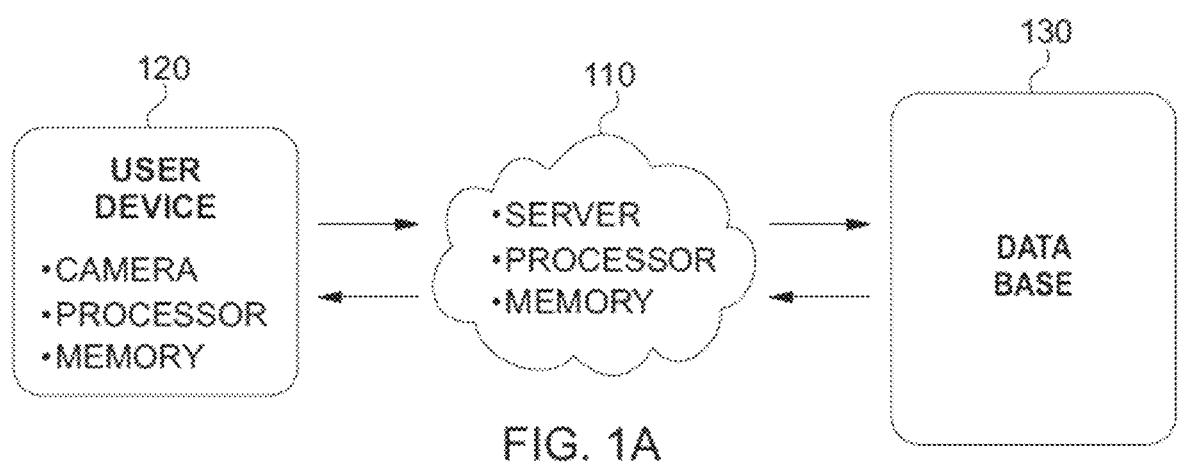
FIG. 1A shows the flow of information between components of the system of the invention.

Various embodiments of the invention are described in detail below. Although specific implementations are described, this is provided for illustration purposes only. A person skilled in the relevant art will recognize that other components and configurations may be used without parting from the spirit and scope of this disclosure.

The terms "3-dimensional", "3-D", "2-dimensional", and "2-D" take on their plain and ordinary meaning.

The term "3-dimensional synthetic item" means a 3-dimensional synthetic model (or 3-dimensional model) of a real-world surgical tool, implant, fastener, or other object.

The term "3-dimensional synthetic model" or "3-dimensional model" means a three-dimensional representation of a real-world object created by and with software used to create the three-dimensional representation in a virtual environment.

The term "synthetic image" in singular or plural form means a computer-generated image of a real-world image or a computer generated virtual rendering of another virtual image.

The invention provides a solution for the present need in the art for systems and methods for surgical item tracking. The invention solves the prior art problems by using an AI-enabled, computer vision system specially programmed to sync with an imager, such as a camera, using a software application running on a mobile computer device having a display (e.g., a mobile phone). The camera provides an image (photograph or video) of a real-world surgical tray and the items contained thereon, which is transmitted via a wired or wireless network, to the software application to: (1) identify the type of tray and the items on the tray; and (2) notify the user if items are missing from the tray. The software application must first be trained to identify a tray and items, i.e., tools, implants, fasteners, and the like, in or on the tray. The training takes place using certain feature vectors combined to create two dimensional matrices, which are themselves combined to create 3-dimensional tensors used to automatically build identification model(s) from 3-dimensional synthetic items. The identification model(s) are created by an AI-enabled computer vision system, which uses 3-dimensional synthetic items previously uploaded to a library database by an administrator, or their employee, contractor, or agent. The software application is trained to identify the items on the tray based on identification model(s) created in the same way, i.e., feature vectors are combined to create 2-dimensional matrices, which are combined to produce 3-dimensional tensors from synthetic instruments previously uploaded to a library database by an administrator, or their employee, contractor, or agent. The identification model(s) are created by a software application by continuously inputting synthetic training datasets comprising random 2-dimensional views of a 3-dimensional synthetic item, wherein (1) the orientation of the 3-dimensional synthetic item, (2) the synthetic light color or intensity illuminating the 3-dimensional synthetic item, and/or (3) the elevation of the 3-dimensional synthetic item above an identified surface, are unique.

Based on the tray classification, the system calls up from a database a list of all real-world items, which should be on the tray including corresponding instrument identification model(s) linked to synthetic items previously uploaded to a library database by an administrator, or their employee, contractor, or agent. Next, the system compares the instrument identification model(s) to the image of the tray to identify items are located on the tray. Finally, the system displays a list of items that were not located in the image of the surgical tray.

Figure 4:
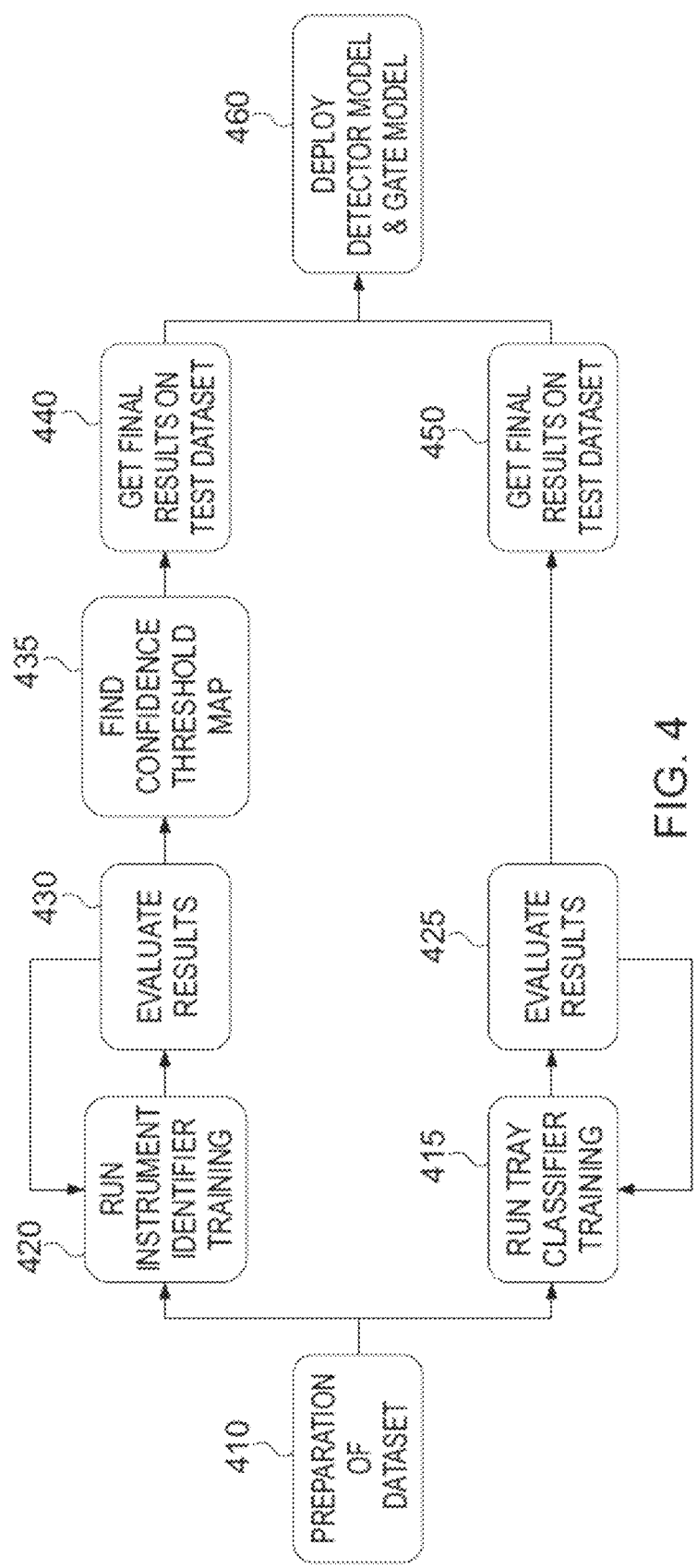
FIG. 4 shows one embodiment for the training of a convolutional neural network which incorporates a confidence threshold map.

FIG. 4 shows a flowchart of a process of an embodiment of system training of the invention. The software application can recognize real-world items from images (photograph or video) because the application has been previously trained with the 3-dimensional synthetic items corresponding with real-world items. In such an embodiment for the data preparation steps, an administrator, or their employee contractor, or agent: (1) selects an item (e.g., tray, tool, implant, fastener, or the like) and creates scenes, and (2) uploads scenes to a 3-D rendering program such as, for example, 3ds Max and/or Unity, and thereafter, and the system (3) renders synthetic images of the device (i.e., 2-dimensional images) and creates correlated synthetic colored masks, (4) provides a dataset to the software application to develop annotated files or to map instrument masks to real world images of instruments, and (5) splits the annotated files into subfiles for layering images. For detector training, the administrator, or their employee, contractor, or agent, or the system can automatically: (1) select a dataset to use for training, (2) prepare a model architecture, (3) select specific augmentations of the images in the dataset to be varied (e.g., color, geometry of item, bounding box size or shape, light level, etc.), (4) set image input size, (5) set data loader settings such as batch size, learning rate, iterations, etc., and (6) deploy the model training in the system and monitors it.

System training results in the creation of a plurality of: (1) tray feature vector(s) linked to specific tray classification(s) and (2) instrument feature vector(s) linked to specific instrument classification(s). The tray feature vector(s) linked to specific tray classifications and the instrument classification vector(s) linked to specific instrument classifications are uploaded to a server located either at the site where images of the real-world trays/instruments are taken, or at a site remote from the site where images of the real-world trays/instruments are taken.

The use of 3-dimensional synthetic items previously uploaded by an administrator, or their employee, contractor, or agent, to the system in order to train the AI-enabled computer vision system solves the real-world feasibility problem previously discussed, by allowing the system to correctly identify, without the need for independent, item-specific markers, all items on a tray with an accuracy of greater than 90%, 91%, 92%, 93%, 94%, 95%, 96%, 97%, 98%, 99%, or even 99.5%. System accuracy is not significantly impacted by images with the real-world items on the tray relocated (or missing) from their typical location/orientation on the tray because the system and method are adapted to manipulate the orientation, shading, and surface texture (e.g., roughness, wear from use, reflectivity, etc.) of the 3-dimensional synthetic items. The system creates hundreds of thousands of 2-dimensional synthetic images of the 3-dimensional synthetic items used to create the necessary linked feature vectors allowing the system to determine whether an items is on or in the tray or not. The invention can be configured to identify real-world items having biologic material on their surfaces, or partially occluded from view. Furthermore, the invention can continuously train the system to reach even higher degrees of accuracy by using more 2-dimensional synthetic images of 3-dimensional synthetic items.

A detailed discussion of the system and methods of the invention is provided below. First, a system overview is discussed. Second, the creation of 3-dimensional synthetic items is outlined. Third, the way the system is trained in discussed. Fourth, the manner by which the system recognizes real-world items in pictures is outlined. Fifth, the way a user may interact with the system is discussed. Sixth, the system components are identified. Seventh, a description of a cloud computing system for the environment of this system occurs. Eighth, the collection and retention of relevant data is disclosed.

System Overview

Figure 1B:
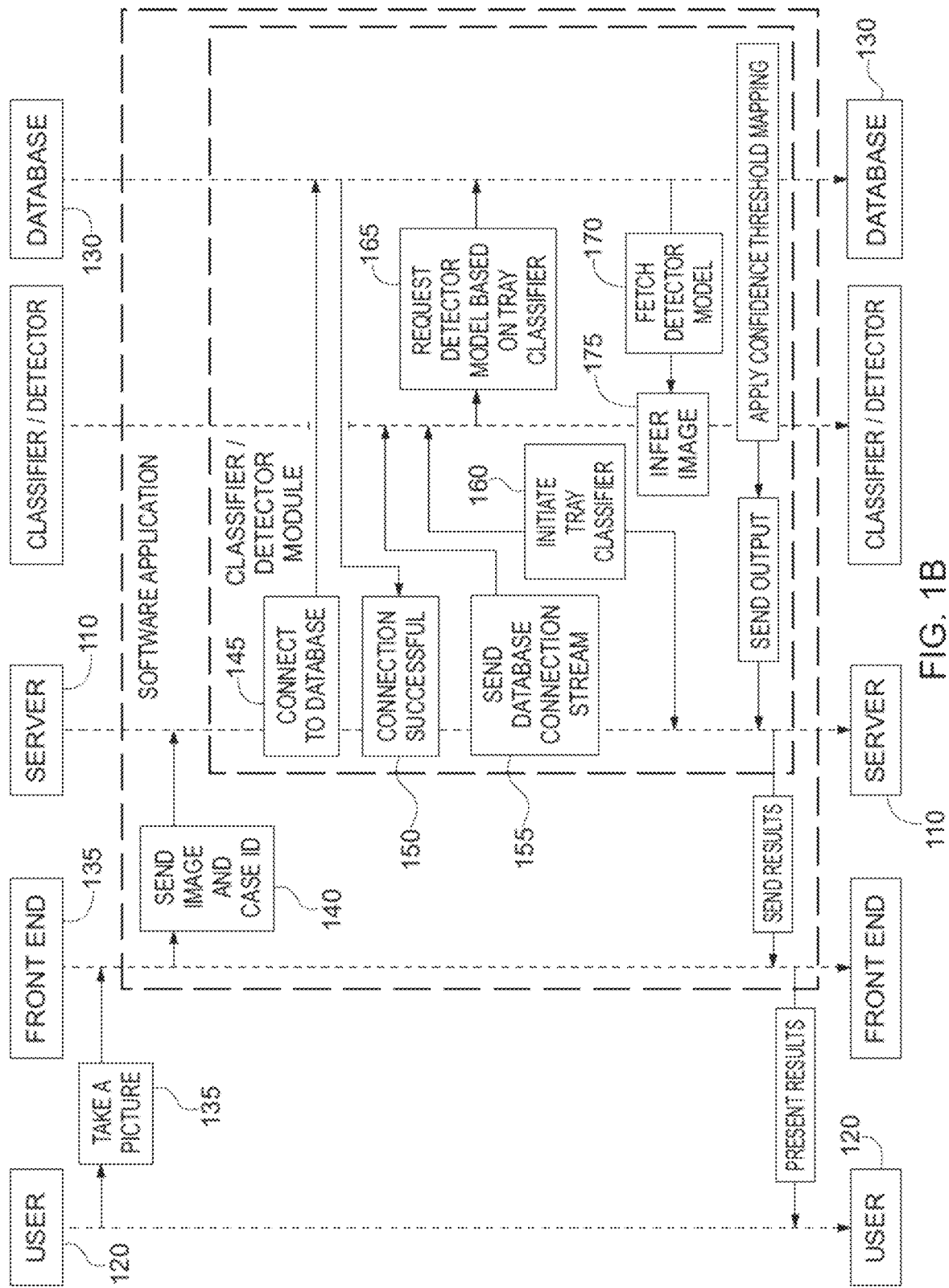
FIG. 1B shows the flow of information between components of the system of the invention.

FIG. 1A shows the system including a server 110 comprising a processor aided by memory that communicates with an image data collection device(s) 120, and database(s) 130. For example, as disclosed in FIG. 1B, a user takes a picture of a surgical tray 135 using an image capture device (e.g., a smartphone). The front end of the software application automatically assigns a case ID and sends 140 the image to the server 110 which deploys the classifier and detector modules of the system. The classifier and detector modules connect 145 to the database(s) 130. The database confirms 150 a successful connection to the server 110. A connection stream 155 comprising the image is sent to the classifier and detector module. The type of tray is classified 160. Once the tray is classified, the classifier and detector module requests instrument detector modules 165 linked to the identified tray classification 160 from the database 130. Linked instrument detector modules 170 are deployed, and the classifier detector module detects the instruments in the image 175. A confidence threshold 180 is applied to each detected instrument. A list of instruments not detected that are linked to the tray classification are determined. Finally, the classified tray along with a list of the detected instruments and missing instruments is then provided to the software application for display on a graphical user interface to the user.

As outlined above, the system proceeds in two phases. First, the system is configured to analyze an image to identify and classify the type of tray in the image. Second, the system is configured then to analyze the trays to determine, what, if any, items are missing from the tray(s) and then to display the results to a user through a graphical user interface. Optionally, the system can store the results in a database for later analysis, such as, for use in auditing. The database(s) contains:

(1) a plurality of 2-dimensional synthetic images of 3-dimensional items, such as, trays and surgical devices, for training an AI-enabled computer vision system, such as a convolutional neural network (CNN), where the synthetic images show: (a) surface texture, (b) item material composition (e.g., metal, plastic, mica, glass, etc.), (c) a size tolerance, which can account for production tolerances or item wear (e.g., a used drill bit may have a slightly smaller circumference than when it was new), and (d) items positions on or in the tray;

(2) a list(s) of tray classification model(s) linking different tray classification model(s) to specific synthetic surgical trays obtained as a result of training the system using the synthetic images;

(3) a plurality of instrument identification model(s) linking different instrument feature vectors to specific instruments obtained as a result of training the system using the synthetic images; and (4) optionally, a plurality of real-life images which are used to train the knowledge of the AI-enabled system.

The information can be uploaded or provided to the database by a system administrator, or their employee, contractor, or agent. Finally, a processor is incorporated into the AI-enabled system: (1) to identify and classify a tray in an image; (2) based on the classification of the tray in the image, to identify a list of items linked to the tray; (3) to analyze the contents of the image to determine whether the items on the specific list are contained in the image; (4) to notify the software application which items are and are not contained in the image; and optionally (5) to determine where any missing items can be located or whether items contained in the image can act as a substitute for missing items.

The invention can operate with tens of thousands of 2-dimensional synthetic images of each 3-dimensional item that must first be created to enable training of the system to dynamically identify items in an image, regardless of the location, orientation, alternate surface texture (e.g., biological material present on the surface of the item), or evidence of use of an item. The system can be taught to recognize different items by identifying and linking feature vectors to different feature vectors and/or specific trays and instruments, implants, tools, or fasteners.

Optionally, numerous real-life images of an object can be used to assist in training the system's ability to recognize different items. Such images are taken with as many item assortments and randomized views of attributes (e.g., lighting, background, camera angle, etc.) as possible. The images of real-life objects are then annotated in a manner similar to the 3-dimensional synthetic items. In an embodiment, such annotation(s) are accomplished using a SENSE software tool. In such an embodiment, bounding boxes are drawn around each item and labeled using the SENSE tool.

Once trained, the system is configured to receive an image (photograph or video) taken by a camera, for example, and to use the image to identify a surgical tray in the image, identify what instruments should be on the surgical tray and whether those instruments are in fact there, and display the results of the analysis (i.e., whether any instruments are missing) to the user for appropriate action in real time.

Creation of Synthetic Items

Figure 2A:
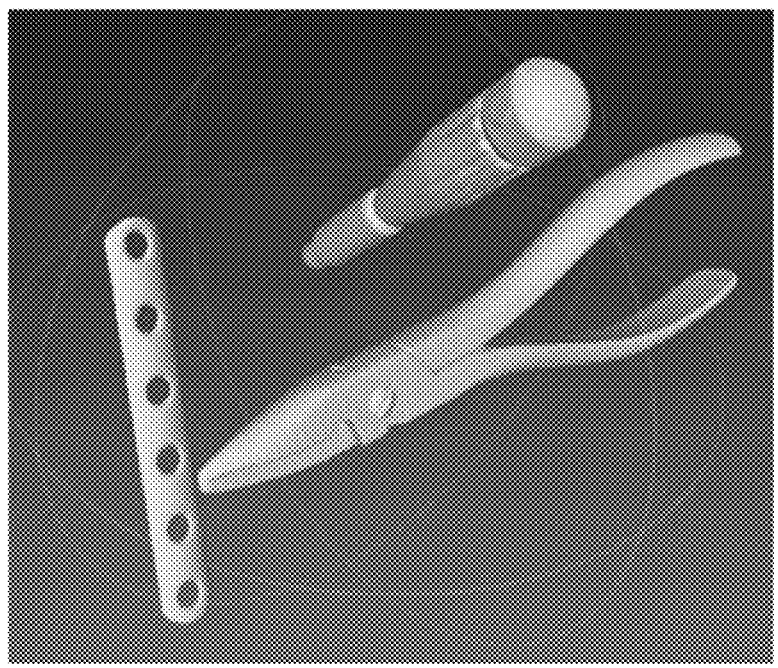
FIG. 2A shows three synthetic items viewed from one vantage point by the system.
Figure 2B:
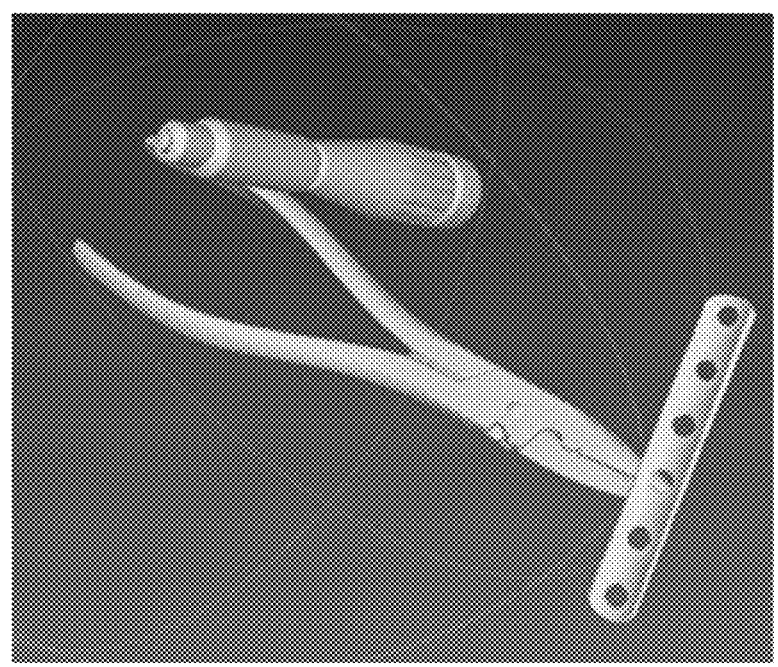
FIG. 2B shows the same synthetic items in FIG. 2A viewed from a different vantage point by the system.

The creation of each 3-dimensional synthetic item of a real-world object is the first step for training the system to recognize features of a real-world object in a photograph taken by a camera. FIGS. 2A and 2B show examples of completed 3-dimensional synthetic items and how those synthetic items can be viewed from different vantage points by a system during training.

The system creates an infinite number of 2-dimensional synthetic images from a 3-dimensional synthetic item, whereby the 2-dimensional synthetic images are used to train the system. The creation of the 3-dimensional synthetic item begins with an administrator, or their employee, contractor, or agent, gathering geometric (shape), surface topography/texture, item material composition, and/or color information about an item to create a preliminary 3-dimensional model. The preliminary 3-dimensional model is refined by the administrator or their employees, contractors, or agents, to create the final 3-dimensional synthetic item, which will be the genesis of all synthetic images of the item used by the system. Conversely, the system can receive 3-D CAD drawing files to create the preliminary 3-dimensional model. Such CAD files can be provided to the system by a manufacturer or distributor of the tray(s) or item(s).

In certain embodiments, the initial information to create the preliminary 3-dimensional model is gathered from multiple different vantage points (poses) with respect to a real-world object or tray. This procedure of capturing views of an item can be referred to as three-dimensional scanning or three-dimensional modeling, which can be preliminarily accomplished using a 3-dimensional modeling system including, for example, one or more 3-D scanners, such as an Artec 3D scanner. Each scanner can include one or more depth cameras, which obtain visual information in the form of one or more streams of images. A depth camera can also include one or more color cameras, which acquire the color information about an item, and one or more Infra-Red (IR) cameras, which can be used in conjunction with an IR structured-light illuminator to preliminarily capture geometry, surface texture, and material information about the item. The color and the IR cameras can be synchronized and geometrically calibrated, thereby allowing the cameras to capture sequences of frames constituted by color images and depth-maps, for which it is possible to provide geometrical alignment. In certain embodiments, the items need to be scanned a minimum of 2 times to capture all the sides of an item. In certain embodiments, the image resolution can be set to 2048×1536 pixels.

The 3-dimensional modeling system, described above, can be used to identify the 3-dimensional locations of visible points on the surface of the real-world object with respect to a reference coordinate system (e.g., a coordinate system having its origin at the depth camera). Thus, a preliminary 3-dimensional model comprising 3-dimensional points can be used to describe a portion of the surface of the real-world object, as well as other surface properties within the field of view of the depth camera by the 3-dimensional modeling system.

The preliminary 3-dimensional model can comprise a collection of 3-dimensional points having x, y, and z coordinates and/or a mesh (e.g., a collection of triangles). The depth camera can also capture, and the preliminary 3-dimensional model can contain, information regarding surface texture, item material composition (e.g., metal, plastic, mica, glass, etc.), and a size tolerance, which can account for production tolerances or item wear (e.g., wear on a used drill bit).

Because 3-dimensional modelling systems are not perfect, image rectification techniques can be used to accommodate distortions to the images from camera lens shape and variations of camera orientation. The 3-dimensional modelling system can also automatically process the preliminary 3-dimensional model to remove "outlier" points due to erroneous measurements (e.g., measurement noise) or to remove structures that are not part of the item or tray, such as a resting surface on which an item is placed. Background items can be removed by, for example, restricting the mapping of points having a depth greater than a particular threshold depth or by detecting a bottommost plane of points.

In some cases, multiple 3-dimensional points and/or meshes can be combined to generate the preliminary 3-dimensional model. The combination can occur by merging module such as, Artec Studio 15 or Blender® software, to generate a preliminary 3-dimensional model (e.g., by using ICP to align and merge the points or meshes and by removing extraneous or spurious points to reduce noise and to manage the size of the 3-dimensional model). In some embodiments, a mesh generation module computes a 3-dimensional mesh from the merged preliminary 3-dimensional model using techniques such as Delaunay triangulation and alpha shapes, and software tools such as MeshLab. The 3-dimensional model can be combined with color information in images obtained using a color camera and can be applied as a texture map (e.g., information about the color of the surface of the model). This creation of a mesh improves segmentation quality in a synthetic image by providing structural information that later facilitates polygonization.

Figure 3:
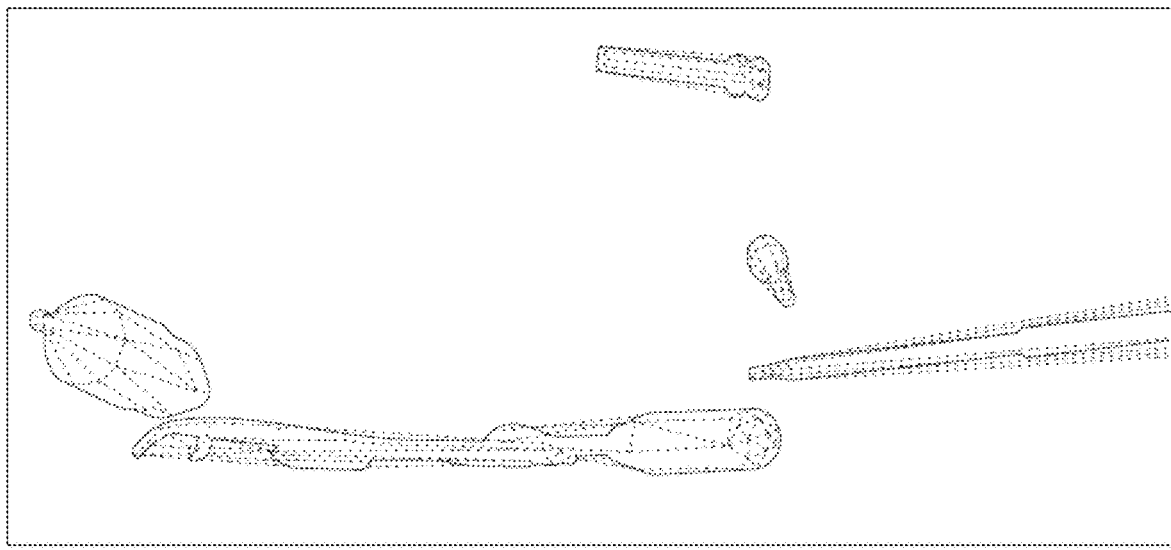
FIG. 3 shows collider bounding boxes (dashed lines) drawn around preliminary 3-D models previously imported into a 3-D modeling application.

Once the preliminary 3-dimensional model is created, it is exported to an application for revising 3-dimensional models in a format, which defines the geometry, position of each vertex, UV position of each texture coordinate vertex, vertex normals, faces that make each polygon defined as a list of vertices, texture coordinates, and other properties for the item or tray. The application for revising 3-dimensional models can be Autodesk 3d Max and the file format may be OBJ format. Once the preliminary 3-dimensional model has been imported into a 3-dimensional modeling application, modifiers are generated and applied to draw collision bounding boxes around the objects depicted in the preliminary 3-dimensional model. Collision bounding boxes are boxes drawn around an object, which contains the entire object. FIG. 3 shows examples of bounding boxes drawn around objects depicted in the preliminary 3-dimensional model. Bounding boxes can be represented as a rectangle with an x and y coordinate, as well as width and height. By drawing a collision boundary box around objects depicted in the preliminary 3-dimensional model, the system has a clear definition of the object. FIG. 3 shows application of such bounding boxes using MassFX which is a toolset that works with Autodesk 3ds Max. While bounding boxes are quick and easy to use, polygonization is an alternative for irregular shapes because polygonization is not restricted to rectangles and squares and therefore captures more lines and angles. Regardless of whether bounding boxes or polygonization is used to map the item(s), labels are applied to the preliminary 3-dimensional model.

The labels identify the type of material, surface texture, and size tolerance information of the item. The labels are either manually or automatically confirmed, supplemented, or assigned to each bounded section of the item or holding tray. For example, the administrator, or their employee, contractor, or agent, can set the relevant bounding box(es) for a tray holder to metallic properties imitating polished aluminum for the metal holders in the tray and micarta material for other plastic holders. Indeed, each synthetic item or tray part may be manually selected via polygon selection, and onto that subset of polygons, a material ID may be manually assigned by the administrator or their employee, contractor, or agent.

In certain embodiments, the manual or automatic creation of the preliminary 3-dimensional model includes a utility shader added to the material information and applied to all synthetic items. This shader generates a unique object mask based on the name of the synthetic item with unique colors assigned to each synthetic item's name. Such an approach allows both the system and users to recognize a synthetic item more easily by synthetic color association.

Furthermore, to assist the system to identify items in different lighting conditions or intensities, a synthetic camera is used to capture different 2-dimensional views of the preliminary 3-dimensional model, or even a 3-dimensional synthetic item, along a path in a set number of frames while dynamically varying the intensity or contrast of the synthetic illumination. A synthetic camera can capture images of various orientation of the preliminary 3-dimensional model, or even a 3-dimensional synthetic item, in a 3-D space. This approach captures thousands of images of the preliminary 3-dimensional model, or even a 3-dimensional synthetic item, in different lighting conditions and different orientation. Using the synthetic images, the optimum lighting condition (i.e., the default lighting condition at which the system can most accurately match the synthetic item to a real-world item regardless of real-world lighting conditions) can be identified. Once identified, the optimum lighting condition is assigned to the different surfaces of each of the preliminary 3-dimensional model, or even a 3-dimensional synthetic item.

Finally, the administrator or their employees, contractors, or agents may manually combine the preliminary 3-dimensional model, or even a 3-dimensional synthetic item, by placing certain ones in specific locations on or in a preliminary 3-dimensional models of a tray to produce a specific complete synthetic tray. The specific complete synthetic tray, all synthetic items associated with that synthetic tray, along with a list of all synthetic items located on the specific complete synthetic tray are then uploaded to the database. In other certain embodiments, the system automatically combines synthetic instruments, implants, tools, or fasteners with synthetic trays.

By manually confirming, supplementing, or assigning a material identification, surface texture, size tolerances, and optimum lighting condition to each polygon of a preliminary 3-D model, a 3-dimensional synthetic item is created, which can be: (1) called up from the database; (2) applied to an image of a tray; and (3) manipulated on the image (e.g., changing the synthetic item's location, orientation, occlusion, surface texture, or light shading on the tray) to further train the system. By using 3-dimensional synthetic items, which can be manipulated to generate the necessary hundreds of thousands of 2-dimensional images, as needed, the system is able to solve the time-problem associated with obtaining hundreds of thousands of real-world images of trays and instruments to train their AI-enabled computer-vision system without the need to independently mark items.

Furthermore, because information related to material, surface texture, size tolerance information, and shading responses has been linked to every individual surface of the synthetic item, the use of 3-dimensional synthetic items to train the system can be significantly varied, resulting in a system with greater recall and precision. For example, the material of a real-world object may be reflective (e.g., metallic). Because material information can be included on the 3-dimensional synthetic item, the system can incorporate glare and reflective elements in its training so that, when the system is deployed for use, the system can identify the real world item shown in a photograph, regardless of the light intensity hitting or reflecting from the instrument.

Once a 3-dimensional synthetic item(s) is/are produced and assigned a unique identification by the system's software, the system can use the 3-dimensional synthetic item(s) to train a deep neural network computer vision object detection model, such as a convolutional neural network (CNN). The computer-vision-assisted deep neural network is trained with the 3-dimensional synthetic items and corresponding unique identifications (e.g., the correct classifications of the items) and optionally real-life images. The parameters of the neural network (e.g., the weights of the connections between the layers) can be implemented using standard processes for training the neural network such as backpropagation, gradient descent, color, geometric, or boundary box augmentation. In addition, the training process can be initialized using parameters from a pre-trained, general-purpose image classification neural network. A portion of this training data may be reserved as cross-validation data to further adjust the parameters during the training process, and a portion may also be reserved as a test dataset to confirm that the network is properly trained.

With this training, the system can identify feature vectors on 3-dimensional synthetic items and images of real-world objects, which can be linked to specific trays and/or instruments. Such identified feature vectors can be uploaded to a server located at the training location or a server that is remote from the training location. Once trained, the system is configured to use the vectors to automatically determine patterns useful in differentiating a real-world object in one image (photograph or video) from another real-world object in another image. Using this approach, the system can recognize a real-world object at different angles, in different lighting conditions, and when object might be occluded by other objects. The system can make this recognition of real-world objects shown in an image in or on a tray, or even of real-world object out of the tray on a surface.

System Training

As previously described, the system is configured to identify, in an image, the presence or absence of an object(s) in or on a surgical tray with significant accuracy because it has been previously trained. The training occurs via a serialized machine learning pipeline. The machine learning pipeline is the end-to-end construct which orchestrates the flow of data into, and output from, a machine learning model or set of multiple models. The system utilizes the 3-dimensional synthetic items to learn to: (1) classify different trays, and (2) identify what instruments are located within the classified tray. The use of 2-dimensional images of 3-dimensional synthetic items can be used to produce an infinite training dataset. The amount of data used to train the system is restricted only by time and the available computing power to create and process synthetic images. By employing the synthetic item(s), the system is configured to create an unending stream of unique synthetic images that can be provided to the system to train it. This infinite training data source provides an item detector, which has a high percentage of recall, meaning the system does not have to guess that often, and a high percentage of precision, meaning that when the system guesses the item in an image, the system is often right.

The process of training any machine learning model involves providing a machine learning algorithm, which is, the learning algorithm, with training data used to construct identification model(s) for surgical tray(s) or item(s) comprised of tensors. In this case, synthetic images are used as training data. In addition, in certain embodiments, real-life images are used to supplement the synthetic images for training purposes. Because the vast majority of the images used to train the system are synthetically created, the following aspects may be easily changed to assist in the system's training: (1) instruments position within the tray can be randomized; (2) instruments that should be on the tray can be randomly chosen to be missing; (3) the elevation of the instruments in relation to the tray may be randomized; (4) the light source may be randomized; (5) instrument distribution within the tray may be randomized (e.g., instruments may be stacked), or (6) the addition of distractor instruments that should not be on the tray. Because of the use of the synthetic items, tens of thousands of randomized synthetic images can be created and used in real time to train the system.

The training process creates and refines the identification model(s). During the training process, the system is provided with synthetic images, and optionally real-life images of objects, e.g., tray(s) or item(s), along with correct results linked to each synthetic, and optionally, real-world, image. The correct results are referred to as a target or a target attribute. The learning algorithm finds patterns in the training data that map the input data attributes to the target. The pattern recognition can be in the form of feature vectors comprised of scalars, which are just single numbers (e.g., reflectivity of a specific physical point). The feature vectors are an array of numbers arranged to identify each individual number by its index in that ordering (e.g., points in space with each element giving a coordinate along a different axis). The feature vectors are combined to form matrices, which are a 2-dimensional array of numbers so each element is identified by two indices instead of just one (e.g., the reflectivity of a screwdriver at coordinates along an axis). Matrices are combined to create tensor(s) which are an array of numbers arranged on a regular grid with a variable number of axes. Feature vectors can be revised by adding additional scalars, matrices can be revised by adding additional feature vectors, and tensors can be revised by adding additional matrices if each have the same shape. Such revisions can be accomplished by the system automatically adding corresponding elements while training. As the system trains, it automatically amends the relevant tensor(s) in a manner that best captures the patterns (i.e., provides the highest recall and precision). The training continues with the updated learning algorithm being exposed to new 2-dimensional synthetic images without the aid of knowing the target or target attributes. Furthermore, because the 2-dimensional synthetic images are created from the 3-dimensional synthetic items, the ability to have the training data include or exclude the correct answer(s) for the system's review can be automatically excluded from being transmitted to the system when training. As a result, not only can the 2-dimensional synthetic images be used to train the system, but they can also serve as a basis to automatically evaluate the system's recall and precision.

FIG. 4 shows an embodiment of a machine learning training module. Both a gate module (i.e., a module that identifies the tray in the image) and a detector module (i.e., a module that identifies the items in the image) are trained. Such training may occur in series or in parallel. Such training may be automatic. In addition, such training may be supervised machine learning and deep learning in that an administrator of the system or an employee, contractor, or agent of the administrator evaluates the results and approves changes to the learning algorithm. As previously discussed, supervised learning involves using an algorithm modeled to an input example to identify target classification(s) (e.g., what instrument(s) are in the image) or numeric value(s) (e.g., how many screw(s) are in the image). In certain embodiments, the target classification and numeric values are linked (e.g., how many screw(s) of a certain type are in the image).

FIG. 4 shows that unique datasets can be automatically prepared by the system 410. Both the tray classifier 415 and the instrument identification 420 modules are trained on 2-dimensional synthetic images. In certain embodiments, the tray classifier 415 and the instrument identification 420 are trained using images of real-world objects. Next, the system results are evaluated for both the instrument identification module 430 and the tray classifier 425. The system provides a confidence threshold 435 for the instrument identifier. The system provides a final identification result for both the instrument identifier 440 and the tray classifier 450. Finally, to the extent that the confidence threshold meet or exceeds a previously set confidence threshold, the system deploys or updates 460 both the instrument identification module and the tray classifier to a database in a server.

Once an identification model has been trained with expected performance, the next step is to assess the prediction results of the identification model in a controlled, close-to-real setting to gain confidence that the model is valid, reliable, and meets business requirements for use. In this step, confidence thresholds of the detector module are set (i.e., the module that identifies whether an item is or is not in an image). In identifying target classification(s) of a real-world object with the detector module, the system assigns a numeric confidence value to each output. This confidence value represents the system's confidence in the prediction. The system determines a correctness of each prediction in the set of predictions and determines a relationship between the confidence scores and the correctness of the test predictions. The system establishes a confidence threshold for the identification model based on the determined relationship and labels. To avoid incorrect designations, the administrator of the system or an employee, contractor, or agent of the administrator designates a minimum confidence threshold and links that minimum confidence threshold to the relevant item in the database. Minimum thresholds can be universal across all items such as a system will only identify a real-world object from an image of a tray if the system identifies the real-world object with more than 90% confidence. Conversely, unique confidence threshold(s) can be linked to individual item(s). For example, the system can be configured to identify a screw in an image with 70% confidence but may be restricted from confirming the presence of a surgical implant in an image unless the confidence value for that identification is greater than 95%.

Once evaluation of the tray classifier model or the identification model is complete, the models are ready for deployment into a production system. In certain embodiments, the production system is deployed as a Web service on a server, which can be called by other components in a target production system such as a network edge device, to get predictive results for what instruments may be located within an image (photograph or video). In some embodiments, the production system will be reimplemented in a programming language that is different from the programming language used to train the system. For example, the system may be trained using Python but implemented in Java.

System Image Recognition

When deployed, the system is able to identify objects, such as surgical instruments, tools, implants, and the like, in images (photograph or video) or real-world surgical trays. In this regard, the deep neural network model first accepts, as an input, a real-world image of a surgical tray taken by a user. In certain embodiments, the imager resolution can be set to 2048×1536 pixels. The image is provided to and processed by the system by first classifying the specific tray. With this information, the system calls up from a database a list of all items that should be located on the tray. Then the system processes the image by comparing it with the identification models and returns a list of detected surgical items with their location on the image or a list of items that should have been but were not located in the image. The system uses the following components to analyze the image: (a) a tray classifier; and (b) a surgical item detector.

The information returned by the tray classifier is used by the system to select the specific surgical item detector(s) intended for a specific tray. The surgical item detector finds a list of specific surgical items in the photo and localizes them (return the coordinates of the smallest rectangle containing the surgical item). Both the classifier and the detector can be based on a convoluted neural network (CNN). In certain embodiments, the surgical item detectors use model architectures such as Faster-RCNN.

In certain embodiments, where surgical items appear similar, a surgical item classifier can be used to support the surgical item detector. In such a situation, the system can pass the portion of a photograph containing problematic items to the surgical item classifier which distinguishes between several similar types of items. As in the case of the tray classifier, the surgical item classifier may be based on a CNN model.

In certain embodiments, the surgical item identification is performed by computing a descriptor which incorporates the unique assigned ID of the synthetic item, where the descriptor is a multi-dimensional vector (i.e., a matrix or a tensor). Common techniques for computing a descriptor of a synthetic item are based on a forward evaluation of a Multi-View Convolutional Neural Network (MV-CNN) or by a Volumetric Convolutional Neural Network (V-CNN). Such networks are usually trained for object classification, and, in some embodiments, the output of the penultimate layer of the network is used as the descriptor.

For example, as previously described, a CNN can be trained using 2-dimensional images of a 3-dimensional synthetic item, as rendered by a view generation module. In operation, the synthesized 2-dimensional images are supplied to a descriptor generator to extract a descriptor or feature vector for each view. The feature vectors for each view may be combined to generate a descriptor for the 2-dimensional images of the synthetic item to classify the views based on the descriptor. In such embodiments, the CNN is used to process the synthesized 2-dimensional images to generate the classification of the object. Generally, a deep CNN processes an image by passing the input image data (e.g., a synthesized 2-dimensional image) through a cascade of layers. These layers can be grouped into multiple stages. The deep CNN may include two stages, a first stage $CNN_1$ made up of N layers (or sub-processes) and a second stage $CNN_2$ made up of M layers. In one embodiment, each of the N layers of the first stage $CNN_1$ can include a bank of linear convolution layers, followed by a point non-linearity layer and a non-linear data reduction layer. In contrast, each of the M layers of the second stage $CNN_2$ may be a fully connected layer. The output p of the second stage is a class-assignment probability distribution. For example, if the entire CNN is trained to assign input images to one of k different classes, then the output of the second stage $CNN_2$ is a vector p that includes k different values, each value representing the probability (or "confidence") that the input image should be assigned the corresponding class.

The values computed by the first stage $CNN_1$ (the convolutional stage) and supplied to the second stage $CNN_2$ (the fully connected stage) are referred to as a descriptor (or feature vector) f. The feature vector or descriptor can be a vector of data having a fixed size which condenses or summarizes the main characteristics of the input image. The first stage $CNN_1$ can be referred to as a feature extraction stage of the classification system.

The architecture of a classifier described above can be applied to classifying multi-view shape representations of synthetic items, if necessary, based on n different 2-D views of the object. For example, the first stage $CNN_1$ can be applied independently to each of the n 2-D views used to represent the synthetic item, thereby computing a set of n feature vectors (one for each of the 2-D views). In some embodiments, the n separate feature vectors are combined using, for example, max pooling wherein, each of the n views is supplied to the first stage $CNN_1$ of the descriptor generator to generate n feature vectors. In max-pooling, the n feature vectors are combined to generate a single combined feature vector or descriptor F, where the j-th entry of the descriptor F is equal to the maximum among the j-th entries among the n feature vectors f. The resulting descriptor F has the same length (or rank) as the n feature vectors f and therefore descriptor F can also be supplied as input to the second stage $CNN_2$ to compute a classification of the object.

Some embodiments of the present invention can also use a voxelization approach to generate a tensor from a volumetric representation of the synthetic item. For example, a CNN may be supplied with tensor that correspond to volumes that intersect with the surface of the synthetic item, where the volumes have a size and shape corresponding to a volumetric 3-D convolutional kernel, rather than 2-D patches of the 2-D view corresponding to the size of the 2-D convolutional kernel.

The extracted tensor can then be supplied to a classifier to classify the object as being a member of one of a particular set of k different classes C, thereby resulting in classification of the target item. This can be done, for example, by supplying the descriptor F to the second stage $CNN_2$, resulting in the vector p of normalized positive numbers representing the class-assignment probability distribution. The index of the largest entry of this vector p is the most likely class for the given shape (i.e., it identifies a surgical item the image most likely contains), with the associated maximum value representing the confidence of this classification. The second stage $CNN_2$ may be referred to as a classification stage of the CNN.

In some embodiments of the invention, the descriptor vector is used to query a database of objects (i.e., surgical items) which are associated with descriptors that were previously computed using the same technique. This database of objects constitutes a set of known surgical items, and a known surgical item corresponding to the current object (e.g., the target item) can be identified by searching for the closest (e.g., most similar) descriptor in the multi-dimensional space of descriptors, with respect to the descriptor of the target item.

In some embodiments of the invention, a $CNN_1$ classifies the target item by using the descriptor F of the target item to retrieve a most similar shape in a data set, rather than by supplying the descriptor F to a second stage $CNN_2$. For example, all of the objects in the training set may be supplied to the first stage $CNN_1$ to generate a set of known descriptors $\{F_{ds}(m)\}$, where the index m indicates a particular labeled shape in the training data. A similarity metric is defined to measure the distance between any two given descriptors (vectors) F and $F_{ds}(m)$. Some simple examples of similarity metrics are a Euclidean vector distance and a Mahalanobis vector distance. In other embodiments, a similarity metric is learned using a metric learning algorithm. A metric learning algorithm may learn a linear or non-linear transformation of feature vector space that minimizes the average distance between vector pairs belonging to the same class (as measured from examples in the training data) and maximizes the average distance between vector pairs belonging to different classes.

In some embodiments of the invention, the administrator of the system or an employee, contractor, or agent of the administrator, can link printed surface characteristics to different surgical items. For example, cervical spine implants can identify the specific height of the implant (e. g., "6 mm", "8 mm" or "12 mm") and may have different colored boxes that designate the left versus right side of the implant. The system may incorporate an optical character recognition module that is capable of identifying the writing or color on the surface of an item. The system can be configured to call up a list of items and the linked printed surface characteristics which has been previously uploaded to the database by the administrator of the system or an employee, contractor, or agent of the administrator. The recognition of the surface printing can be used by the system to increase or decrease the numeric confidence value of the identified item.

Once the target item has been identified, data about its identity may be retrieved from, for example, the library database. The retrieved data may include, for example, the expected location on the tray, a reference synthetic item (e.g., the expected shape of the item), one or more defect detection models (e.g., models, such as a second convolutional neural networks, trained to detect defects in the item) and the like.

Display Output

The system continues until all of the target items are identified. Before, during or after all the target items are identified, the system retrieves the list of all the items that should be included on the tray. The system compares the list of identified items that exceed the set confidence value to the list of items that should be on the tray and determines what items it is confident are on the tray and what items are not. The system then displays to the user on a graphical user interface, the list of items located on the tray and the list of items that were not identified as being on the tray. Optionally, the system can display the name of the tray, the location of the items located on the tray, and the location of where missing items should have resided on the tray. The user can then interact with the system and either manually classify missing items as actually being on the tray, confirm that items are in fact missing from the tray and/or request the system identify potential alternates to the missing items.

System Interaction with Users

Although the disclosed system may proceed automatically, individual(s) and/or team(s) can interact with users. For example, in one embodiment, a user can audit or change the system's identification of items on the surgical tray with such information being transmitted back to the administrator of the system or an employee, contractor, or agent of the administrator for incorporation into additional system training. This section describes non-limiting, exemplary embodiments of such interactions in which a user may review, approve, or change any aspect of the tray or items identified by the system.

User Login

The first step of the software application is for the user to login. In one embodiment, the system provides for multi-role support. For example, the user can be a healthcare administrator, nurse, doctor/surgeon, a representative of the company that manufactures an item that should be included on the tray, or an insurance professional.

The user begins by visiting a website or loading a computer application. A server determines if this is the first visit by the user. If the server determines this is a subsequent visit, prior general information (e.g., name, contact information, access authorization, etc.) is loaded. If this is the first visit by the user, the same general information is collected. Once the user is identified, they are permitted to sign into the application. Upon signing in, the user arrives at the landing page. In one non-limiting embodiment, the landing page is dynamic and can display different information depending on the role of the user (i.e., an insurance professional would be presented with the different landing page than a surgeon, who would themselves see a different page from a hospital administrator).

Equipment Selection

In one embodiment, the ability to review the list of trays and items contained thereon and/or missing depends on the role of the user. For example, if the user signs in as a nurse, the system can restrict user access to only view a list of trays and items contained thereon for the upcoming surgery. Conversely, a hospital administrator can be permitted to not only view the upcoming surgery, but also a list of trays and equipment used in all prior surgeries by the relevant surgeon. Furthermore, certain users, such as medical device sales representatives can be restricted to see the contents of trays that are supposed to contain their products, which would allow those representatives to identify when their products are missing from trays.

In another embodiment, the system can further include an option to audit the items on the tray. In such an embodiment, a user, such as a hospital administrator, can first view the patient's case and a list of the required trays and items. The user can then view whether multiple pieces of the same equipment are located on other trays. In this regard, the user can identify potential areas of waste.

System Components

Figure 5:
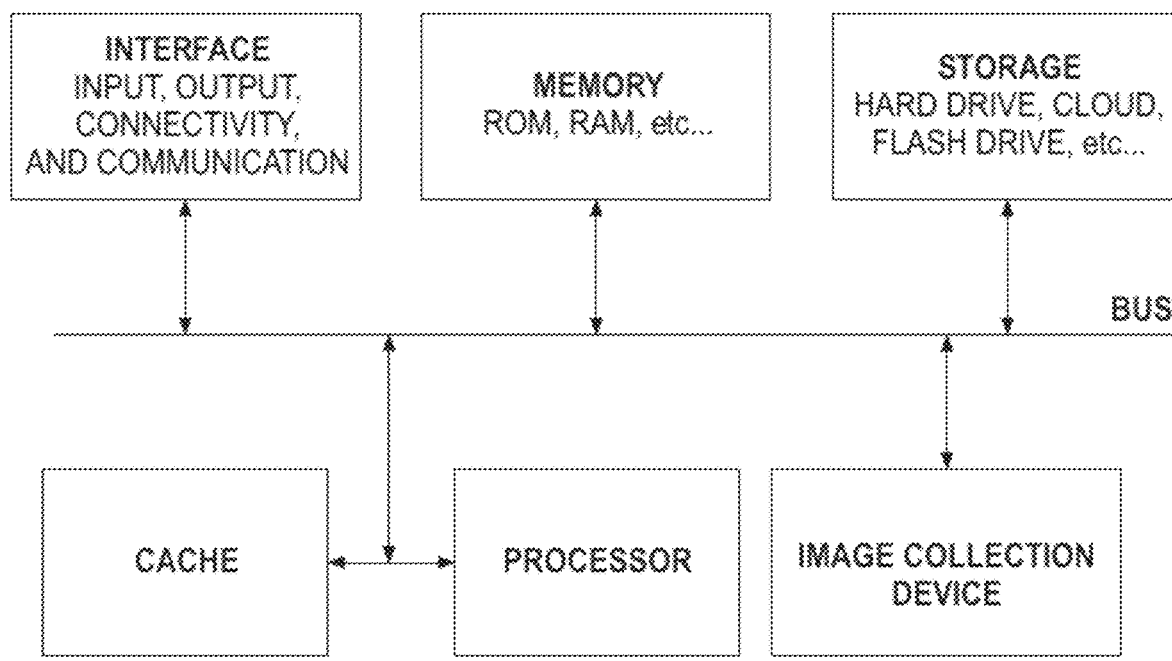
FIG. 5 shows the hardware components of the system of the invention.

FIG. 5 shows an embodiment of the system components. A non-limiting embodiment of the system includes a general-purpose computing device, including a processing unit (CPU or processor), and a system bus that couples various system components including the system memory such as read only memory (ROM) and random-access memory (RAM) to the processor. The system can include a storage device connected to the processor by the system bus. The system can include interfaces connected to the processor by the system bus. The system can include a cache of high-speed memory connected directly with, in close proximity to, or integrated as part of the processor. The system can copy data from the memory and/or a storage device to the cache for quick access by the processor. In this way, the cache provides a performance boost that avoids processor delays while waiting for data. These and other modules stored in the memory, storage device or cache can control or be configured to control the processor to perform various actions. Other system memory may be available for use as well. The memory can include multiple different types of memory with different performance characteristics.

Computer Processor

The invention can operate on a computing device with more than one processor or on a group or cluster of computing devices networked together to provide greater processing capability. The processor can include any general-purpose processor and a hardware module or software module, stored in an external or internal storage device, configured to control the processor, as well as a special-purpose processor where software instructions are incorporated into the actual processor design. The processor can be an entirely self-contained computing system, containing multiple cores or processors, a bus, memory controller, cache, etc. A multi-core processor can be symmetric or asymmetric.

For clarity purposes, a system embodiment can include individual functional blocks including functional blocks labeled as a "processor". The functions such blocks represent may be provided through the use of either shared or dedicated hardware, including, but not limited to, hardware capable of executing software and hardware, such as a processor, that is purpose-built to operate as an equivalent to software executing on a general-purpose processor. For example, the functions of one or more processors may be provided by a single shared processor or multiple processors and use of the term "processor" should not be construed to refer exclusively to hardware capable of executing software. Illustrative embodiments may include microprocessor and/or digital signal processor (DSP) hardware, read-only memory (ROM) for storing software performing the operations discussed below, and random-access memory (RAM) for storing results. Very large-scale integration (VLSI) hardware embodiments, as well as custom VLSI circuitry in combination with a general purpose DSP circuit, may also be provided.

System Bus

The system bus can be any of several types of bus structures including a memory bus or memory controller, a peripheral bus, and a local bus using any of a variety of bus architectures. A basic input/output (BIOS) stored in ROM or the like, can provide the basic routine that helps to transfer information between elements within the computing device, such as during start-up.

Storage Device

The computing device can further include a storage device such as a hard disk drive, a magnetic disk drive, an optical disk drive, a solid-state drive, a tape drive, or the like. Like the system memory, a storage device may be used to store data files, such as location information, menus, software, wired and wireless connection information (e.g., information that can enable the mobile device to establish a wired or wireless connection, such as a USB, Bluetooth or wireless network connection), and any other suitable data. Specifically, the storage device and/or the system memory can store code and/or data for carrying out the disclosed techniques among other data.

In one aspect, a hardware module that performs a function includes the software component stored in a non-transitory computer-readable medium in connection with the necessary hardware components, such as the processor, bus, display, and so forth, to carry out the function. The basic components are known to those of skill in the art and appropriate variations are contemplated depending on the type of device, such as whether the device is a small, handheld computing device, a desktop computer, or a computer server.

Although an embodiment described herein employs cloud computing and cloud storage, it should be appreciated by those skilled in the art that other types of computer readable media which can store data that are accessible by a computer, such as magnetic cassettes, flash memory cards, digital versatile disks, cartridges, random access memories (RAMS), read only memory (ROM), a cable or wireless signal containing a bit stream and the like, may also be used in the operating environment. Furthermore, non-transitory computer-readable storage media as used herein include all computer-readable media, with the sole exception being a transitory propagating signal per se.

Interface

To enable user interaction with the computing device, an input device represents any number of input mechanisms, such as a microphone for speech, a web camera for video, a touch-sensitive screen for gesture or graphical input, keyboard, mouse, motion input, speech and so forth. An output device can also be one or more of several output mechanisms known to those of skill in the art such as a display screen, speaker, alarm, and so forth. In some instances, multimodal systems enable a user to provide multiple types of input to communicate with the computing device. The communications interface generally governs and manages the user input and system output. Furthermore, one interface, such as a touch screen, may act as an input, output and/or communication interface.

There is no restriction on operating on any hardware arrangement and therefore the basic features here can be substituted for improved hardware or firmware arrangements as they are developed.

Image Data Collection Device

The system includes at least one image collection device for obtaining real world pictures of the relevant surgical trays. In certain embodiments, the image data collection device can be a camera capable of capturing photographs or video of real-world objects.

In one non-limiting embodiment, the image data collection device can be mounted on a wearable device, such as a headset or glasses. The wearable device can include a wearable data collection device configured to alarm or vibrate if the items are identified as missing from surgical trays, which may require immediate intervention prior to the procedure.

In one embodiment, the image data collection device includes electronic components for wired or wireless communication with the system. As a result, the data collection device can avoid interference with the procedure. In one embodiment, the image data collection device is replaceable or added to, such that different image data collection devices can be removed, which can allow the image data collection device to be cleaned.

In another embodiment, the image data collection device can include an embedded monitoring component that is configured to verify the identity of the user and monitor the procedure. For example, the data collection device can employ facial recognition software or fingerprint analysis to confirm the identity of the user at set intervals or continuously.

The system can include more than one image data collection device. Indeed, the system may include 2, 3, 4, 5, 6, 7, 8, 9, or 10 image data collection devices. For example, the surgeons and nurses can all wear cameras.

In one embodiment, the image data collection devices can be contained within a tamper-proof housing to prevent the subject from removing the image data collection device.

Software Operations

The logical operations of the various embodiments disclosed are implemented as: (1) a sequence of computer implemented steps, operations, or procedures running on a programmable circuit within a general use computer, (2) a sequence of computer implemented steps, operations, or procedures running on a specific-use programmable circuit; and/or (3) interconnected machine modules or program engines within the programmable circuits. The system can practice all or part of the recited methods, can be a part of the recited systems, and/or can operate according to instructions in the recited non-transitory computer-readable storage media. Such logical operations can be implemented as modules configured to control the processor to perform functions according to the programming of the module. For example, if a storage device contains modules configured to control the processor, then these modules may be loaded into RAM or memory at runtime or may be stored as would be known in the art in other computer-readable memory locations. Having disclosed some components of a computing system, the disclosure now turns to a description of cloud computing, which is the preferred environment of the invention.

Cloud System

Cloud computing is a type of Internet-based computing in which a variety of resources are hosted and/or controlled by an entity and made available by the entity to authorized users via the Internet. A cloud computing system can be configured, wherein a variety of electronic devices can communicate via a network for purposes of exchanging content and other data. The system can be configured for use on a wide variety of network configurations that facilitate the intercommunication of electronic devices. For example, each of the components of a cloud computing system can be implemented in a localized or distributed fashion in a network.

Cloud Resources

The cloud computing system can be configured to include cloud computing resources (i.e., "the cloud"). The cloud resources can include a variety of hardware and/or software resources, such as cloud servers, cloud databases, cloud storage, cloud networks, cloud applications, cloud platforms, and/or any other cloud-based resources. In some cases, the cloud resources are distributed. For example, cloud storage can include multiple storage devices. In some cases, cloud resources can be distributed across multiple cloud computing systems and/or individual network enabled computing devices. For example, cloud computing resources can communicate with a server, a database, and/or any other network enabled computing device to provide the cloud resources.

In some cases, the cloud resources can be redundant. For example, if cloud computing resources are configured to provide data backup services, multiple copies of the data can be stored such that the data is still available to the user even if a storage resource is offline, busy, or otherwise unavailable to process a request. In another example, if a cloud computing resource is configured to provide software, then the software can be available from different cloud servers so that the software can be served from any of the different cloud servers. Algorithms can be applied such that the closest server or the server with the lowest current load is selected to process a given request.

User Terminal

A user interacts with cloud computing resources through user terminals or linked devices connected to a network by direct and/or indirect communication. Cloud computing resources can support connections from a variety of different electronic devices, such as servers; desktop computers; mobile computers; handheld communications devices (e. g., mobile phones, smart phones, tablets); set top boxes; network-enabled hard drives; and/or any other network-enabled computing devices. Furthermore, cloud computing resources can concurrently accept connections from and interact with multiple electronic devices. Interaction with the multiple electronic devices can be prioritized or occur simultaneously.

Cloud computing resources can provide cloud resources through a variety of deployment models, such as public, private, community, hybrid, and/or any other cloud deployment model. In some cases, cloud computing resources can support multiple deployment models. For example, cloud computing resources can provide one set of resources through a public deployment model and another set of resources through a private deployment model.

In some configurations, a user terminal can access cloud computing resources from any location where an Internet connection is available. However, in other cases, cloud computing resources can be configured to restrict access to certain resources such that a resource can only be accessed from certain locations. For example, if a cloud computing resource is configured to provide a resource using a private deployment model, then a cloud computing resource can restrict access to the resource, such as by requiring that a user terminal access the resource from behind a firewall.

Service Models

Cloud computing resources can provide cloud resources to user terminals through a variety of service models, such as Software as a Service (SaaS), Platforms as a service (PaaS), Infrastructure as a Service (IaaS), and/or any other cloud service models. In some cases, cloud computing resources can provide multiple service models to a user terminal. For example, cloud computing resources can provide both SaaS and IaaS to a user terminal. In some cases, cloud computing resources can provide different service models to different user terminals. For example, cloud computing resources can provide SaaS to one user terminal and PaaS to another user terminal.

User Interaction

In some cases, cloud computing resources can maintain an account database. The account database can store profile information for registered users. The profile information can include resource access rights, such as software the user is permitted to use, maximum storage space, etc. The profile information can also include usage information, such as computing resources consumed, data storage location, security settings, personal configuration settings, etc. In some cases, the account database can reside on a database or server remote to cloud computing resources such as servers or database.

Cloud computing resources can provide a variety of functionality that requires user interaction. Accordingly, a user interface (UI) can be provided for communicating with cloud computing resources and/or performing tasks associated with the cloud resources. The UI can be accessed via an end user terminal in communication with cloud computing resources. The UI can be configured to operate in a variety of client modes, including a fat client mode, a thin client mode, or a hybrid client mode, depending on the storage and processing capabilities of cloud computing resources and/or the user terminal. Therefore, a UI can be implemented as a standalone application operating at the user terminal in some embodiments. In other embodiments, a web browser-based portal can be used to provide the UI. Any other configuration to access cloud computing resources can also be used in the various embodiments.

Collection of Data

In some configurations, during the implementation of the system or method described above, a storage device or resource can be used to store relevant data transmitted from the image data collection device(s). Such information may be used by the system to further refine the identification of items on a surgical tray in the future. In such an embodiment, the system may engage in additional machine learning. Such learning will permit more efficient item identification in the future.

In another embodiment, the image data collection device (s) may capture specific tendencies of the individual(s) and/or team(s) performing the procedure. The system may utilize such information to immediately or in the future suggests adjustments to the items on the tray and/or needed equipment. Indeed, the system may be a dynamic system that through use learns the preferences and tendencies of the individual(s) and/or team(s) performing the procedure. By learning such preferences and/or tendencies the system may increase the efficiencies and/or lower the cost of the procedures. For example, the system may recommend that certain items that are never used by the team be removed from future trays.

The system also contemplates that this gathered data might include personal and/or sensitive data in some instances. The system further contemplates that the entities responsible for the collection, analysis, disclosure, transfer, storage, or other use of such data should implement and consistently use privacy policies and practices that are generally recognized as meeting or exceeding industry or governmental requirements for maintaining personal information data private and secure. For example, user data should be collected only for legitimate and reasonable uses of the entity and not shared or sold outside of those legitimate uses. Further, such collection should occur only after the informed consent of the subjects. Additionally, such entities should take any needed steps for safeguarding and securing access to such personal data and ensuring that others with access to the personal data adhere to their privacy and security policies and procedures. Further, such entities can subject themselves to evaluation by third parties to certify their adherence to widely accepted privacy policies and practices.

While this subject matter has been disclosed with reference to specific embodiments, it is apparent that other embodiments and variations can be devised by others skilled in the art without departing from the true spirit and scope of the subject matter described herein. The appended claims include all such embodiments and equivalent variations.

What is claimed is:

1. A system for dynamically identifying a surgical tray and items contained thereon, the system comprising:
 a software application, the software application operating on a mobile computer device or a computer device in communication with at least one image data collection device configured to produce an image of the surgical tray, the software application is configured to receive the image of the surgical tray from the image data collection device and then communicate the image through a wired and/or wireless communication network to a server located at a site where the surgical tray is located or at a location remote from the site; and
 a processor in communication through the wired and/or wireless communication network with the software application, as well as the server, the processer is configured to call up from a library database of the system, upon communication of the image to the server:
  a plurality of tray identification models comprised of tray tensors, the tray identification models uploaded to the library database of the system;
 whereby the processor is configured to:
  analyze the image of the surgical tray and classify the type of tray in the image based on the tray identification models applied to the image,
  call up from the library database:
   a list of items linked to the classification of the type of tray, and a plurality of instrument identification models comprised of instrument tensors generated using a 3-dimensional synthetic item that exists entirely in a virtual environment, the instrument identification models linked to the items and uploaded to the library database of the system;
  analyze the image and identify the type of items in the image based on the instrument identification models,
  compare the classified items to the list of items linked to the classified tray to determine any missing items, and
  notify the software application of the classified items and any missing items.

2. The system of claim 1 wherein the image data collection device is a camera.

3. The system of claim 1 wherein the image data collection device is mounted on a wearable device.

4. The system of claim 1, wherein the tray identification models comprised of tray tensors and the instrument identification models comprised of instrument tensors are generated using a computer vision-driven artificial intelligence network trained using 2-dimensional views of the 3-dimensional synthetic item, as rendered by a view generation module.

5. The system of claim 4, wherein the artificial intelligence network is a convolutional neural network.

6. The system of claim 4, wherein the computer vision-driven artificial intelligence network is continuously trained using 2-dimensional views of the 3-dimensional synthetic item, as rendered by a view generation module.

7. A method for identifying a surgical tray and items contained thereon, the method comprising:
  receiving an image of the surgical tray and items contained thereon from an image data collector connected to a server or a remote server using a software application operating on a mobile computer device or a computer device that may be synced with the mobile computer device, and wherein the mobile computer device or the computer device communicate through a wired and/or wireless communication network with the server at a site the surgical tray is located at or with a remote server in a location that is remote to the site and in communication with the server;
  upon receiving the information, calling up from a database using a processor:
    a plurality of tray identification models comprised of tray tensors, wherein the tray identification models including tray names and items intended to be contained in the trays have been previously uploaded to the database;
  analyzing the image and classifying the type of tray in the image based on the tray identification models;
  upon classifying the tray, calling up from the database a plurality of instrument identification models linked to the classification of the tray and comprised of instrument tensors generated using a 3-dimensional synthetic item that exists entirely in a virtual environment, the instrument identification models including: (a) surface texture, (b) item material composition, and (c) a size tolerance; and a list of items linked to the tray classification;
  analyzing the image and classifying the type of items in the image based on the instrument identification models;
  comparing the classified items to the list of items linked to the classified tray to determine any missing items, and
  notifying the software application of the classified items and any missing items.

8. The method of claim 7 wherein the image data collection device is a camera.

9. The method of claim 7 wherein the image data collection device is mounted on a wearable device.

10. The method of claim 7, wherein the tray identification models comprised of tray tensors and the instrument identification models comprised of instrument tensors are generated using a computer vision-driven artificial intelligence network trained using 2-dimensional views of the 3-dimensional synthetic item, as rendered by a view generation module.

11. The method of claim 10, wherein the artificial intelligence network is a convolutional neural network.

12. The method of claim 10, wherein the computer vision-driven artificial intelligence network is continuously trained using 2-dimensional views of the 3-dimensional synthetic items rendered by a view generation module.

* * * * *